(12) United States Patent
Sundaram (10) Patent No.: US 11,473,044 B2
(45) Date of Patent: Oct. 18, 2022

(54) PHOTOBIOREACTOR WITH ANNULAR CHAMBERS

(71) Applicant: ExxonMobil Technology and Engineering Company, Annandale, NJ (US)

(72) Inventor: Narasimhan Sundaram, Annandale, NJ (US)

(73) Assignee: EXXONMOBILE TECHNOLOGY AND ENGINEERING COMPANY, Annandale, NJ (US)

( * ) Notice: Subject to any disclaimer, the term of this patent is extended or adjusted under 35 U.S.C. 154(b) by 311 days.

(21) Appl. No.: 16/891,141

(22) Filed: Jun. 3, 2020

(65) Prior Publication Data
US 2021/0017480 A1    Jan. 21, 2021

Related U.S. Application Data

(60) Provisional application No. 62/876,232, filed on Jul. 19, 2019.

(51) Int. Cl.
| C12M 1/00 | (2006.01) |
| C12N 1/12 | (2006.01) |
| C10L 1/02 | (2006.01) |

(52) U.S. Cl.
CPC ............... C12M 21/02 (2013.01); C10L 1/02 (2013.01); C12M 29/00 (2013.01); C12M 31/08 (2013.01); C12N 1/12 (2013.01); C10L 2200/0469 (2013.01); C10L 2290/26 (2013.01)

(58) Field of Classification Search
CPC ............... C10L 1/02; C10L 2200/0469; C10L 2290/26; C12M 21/02; C12M 23/02; C12M 23/22; C12M 23/34; C12M 29/00; C12M 31/08; C12M 31/10; C12N 1/12
See application file for complete search history.

(56) References Cited

U.S. PATENT DOCUMENTS

| 8,586,353 | B2 | 11/2013 | Woods et al. |
| 9,523,070 | B2 * | 12/2016 | Erickson ................ C12M 31/04 |
| 9,790,458 | B2 * | 10/2017 | Podsiadlo ............. C12M 41/10 |
| 9,896,652 | B2 | 2/2018 | Ashley et al. |
| 10,149,422 | B2 | 12/2018 | Tippery et al. |

* cited by examiner

*Primary Examiner* — Ellen M McAvoy
*Assistant Examiner* — Chantel L Graham
(74) *Attorney, Agent, or Firm* — Kristina Okafor (57) ABSTRACT

A photobioreactor includes one or more annular chambers concentrically positioned about a central axis, and an algae slurry contained within the one or more annular chambers.

17 Claims, 3 Drawing Sheets

PHOTOBIOREACTOR WITH ANNULAR CHAMBERS

CROSS-REFERENCE TO RELATED APPLICATIONS

This application claims priority to U.S. Provisional Application No. 62/876,232 filed Jul. 19, 2019, which is herein incorporated by reference in its entirety.

BACKGROUND OF THE INVENTION

Concerns about climate change, carbon dioxide ($CO_2$) emissions, and depleting mineral oil and gas resources have led to widespread interest in the production of biofuels from algae and microalgae. As compared to other plant-based feedstocks, algae have higher $CO_2$ fixation efficiencies and growth rates, and growing algae can efficiently utilize wastewater and industrial gases as nutrient sources. The most developed method for extracting biofuels from microalgae is converting their stored lipids into renewable diesel and jet fuel.

Algae biomass is generally grown in a water slurry contained in a photobioreactor (PBR) using photosynthetic algae strains. Algae are classified as photoautotrophic organisms, or organisms that can survive, grow and reproduce with energy derived entirely from the sun through the process of photosynthesis. Photosynthesis is essentially a carbon recycling process through which inorganic $CO_2$ is combined with solar energy, other nutrients, and cellular biochemical processes to synthesize carbohydrates and other compounds critical to life. Photosynthesis absorbs light in a limited range of the total solar spectrum, only in the wavelength range of 400-700 nm, which only represents about half of the total solar energy.

Effective PBR designs must be able to sustain high-density cultures while enabling efficient light delivery and gas exchange. The most common types of PBRs used in algal cultivation are open raceway ponds and tubular-type enclosed reactors. While these designs do have respective advantages, both are faced with fundamental limitations in delivery of sufficient light to maintain high photosynthetic rates. Uneven light distribution causes the algae to be overexposed at the surface and underexposed below the light penetration depth.

SUMMARY OF THE INVENTION

The present disclosure is related to biofuel production from algae and, more particularly, to photobioreactors including one or more annular chambers designed to grow algae.

In some embodiments a photobioreactor is disclosed that includes one or more annular chambers concentrically positioned about a central axis, and an algae slurry contained within the one or more annular chambers.

In some embodiments, a method of growing algae for biofuel production is disclosed and includes introducing an algae slurry into one or more annular chambers concentrically positioned about a central axis of a photobioreactor, introducing a gas into the one or more annular chambers via a gas flow manifold fluidly coupled to the one or more annular chambers, and impinging light on the algae slurry contained within the one or more annular chambers.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to biofuel production from algae and, more particularly, to photobioreactors including one or more annular chambers designed to grow algae.

Figure 1A:
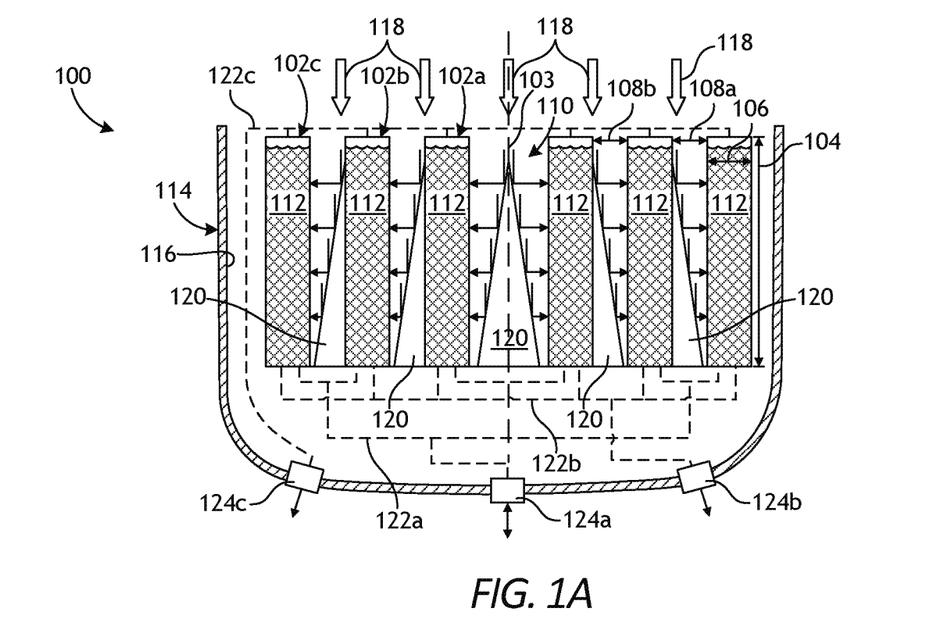
FIGS. 1A and 1B are cross-sectional side and top views, respectively, of an example photobioreactor that may incorporate the principles of the present disclosure.
Figure 1B:
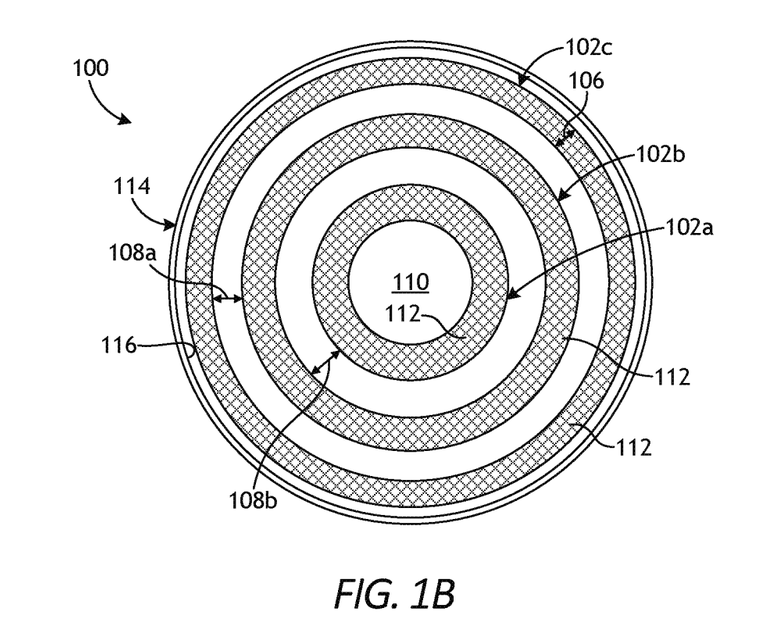

FIGS. 1A and 1B are cross-sectional side and top views, respectively, of an example photobioreactor 100 that may incorporate the principles of the present disclosure. The photobioreactor 100 may be configured to cultivate, grow, and harvest algae to be converted into biofuels. As illustrated, the photobioreactor 100 includes or otherwise defines a plurality of annular chambers, shown as a first annular chamber 102a, a second annular chamber 102b, and a third annular chamber 102c. The annular chambers 102a-c comprise cylindrical structures that are capable of being nested concentrically within one another about a central axis 103. In the illustrated embodiment, the first annular chamber 102a is concentrically nested within and radially offset from the second annular chamber 102b, and the second annular chamber 102b is concentrically nested within and radially offset from the third annular chamber 102c. While the photobioreactor 100 is described herein as including three annular chambers 102a-c, more or less than three annular chambers 102a-c may be employed in the photobioreactor 100, without departing from the scope of the disclosure.

Each annular chamber 102a-c exhibits a height 104 (FIG. 1A) and a depth 106 (i.e., the distance between inner and outer radial surfaces). In some embodiments, the height 104 of each annular chamber 102a-c may be the same. In other embodiments, however, the height 104 of one or more of the annular chambers 102a-c may be different. Similarly, in some embodiments, the depth 106 of each annular chamber 102a-c may be the same, but in other embodiments the depth 106 of one or more of the annular chambers 102a-c may be different, without departing from the scope of the disclosure.

The third annular chamber 102c may exhibit a diameter large enough to concentrically accommodate the second annular chamber 102b such that a first gap 108a is defined between the inner radial surface of the third annular chamber 102c and the outer radial surface of the second annular chamber 102b. Similarly, the second annular chamber 102b may exhibit a diameter large enough to concentrically accommodate the first annular chamber 102a such that a second gap 108b is defined between the inner radial surface of the second annular chamber 102b and the outer radial surface of the first annular chamber 102a. In some embodiments, the gaps 108a,b may exhibit the same dimension (distance), but may alternatively exhibit different dimensions (distances), without departing from the scope of the disclosure. The innermost first annular chamber 102a may define a central opening 110. As described in more detail below, the gaps 108a,b and the central opening 110 may facilitate light propagation (dissemination) along the entire height 104 of each annular chamber 102a-c.

In some embodiments, the diameter, the height, and the depth of the annular chambers 102a-c may each range between about 1 foot to about 20 feet, and the width of the gaps 108a,b may range between about ⅓ inch and about 6 inches. It should be noted, however, that dimensions of any of the structural components of the photobioreactor 100 can vary and will generally depend on the specific application and desired operating parameters of the photobioreactor 100. Accordingly, the diameter, the height 104, and the depth 106 of any of the annular chambers 102a-c, and the size (width) of the gaps 104a,b can be varied and otherwise optimized to meet specific operating parameters or desired outcomes. Accordingly, nothing in this disclosure should be interpreted as limiting the size or dimensions of any of the structural components of the photobioreactor 100.

Each annular chamber 102a-c may have contained therein an aqueous culture of photosynthetic microorganisms, referred to herein as an algae slurry 112. The algae slurry 112 may generally comprise water combined with an algae feedstock, maintained in conditions suitable for the growth, and harvesting of algae for biofuel production.

Algal sources for the algae growing within the algae slurry 112 can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui,* and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella,* and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema,* and *Xenococcus* species.

The annular chambers 102a-c may be made of any transparent or translucent material that permits the penetration (propagation) of light therethrough to provide photonic energy input for the algae slurry 112 contained therein. Suitable materials for the annular chambers 102a-c include, but are not limited to, glass, a polymer (e.g., polycarbonate, etc.), acrylic, a composite material (e.g., fiberglass), or any combination thereof.

In some embodiments, the annular chambers 102a-c may be made of a rigid or semi-rigid material that allows the annular chambers 102a-c to self-support under the weight of itself and the algae slurry 112 contained therein. In other embodiments, however, the annular chambers 102a-c may be made of a flexible or non-rigid material, such as a bag or sheet material that will simply contain the algae slurry 112 but must be at least partially structurally supported against gravitational forces.

In the illustrated embodiment, the annular chambers 102a-c exhibit a circular cross-section. In contrast to flat-walled vessels or chambers used in other photobioreactors, the curved outer surfaces of the annular chambers 102a-c may prove advantageous in dissipating hydrostatic forces and hoop stresses caused by the loading of the algae slurry 112. The curved outer surfaces of the annular chambers 102a-c may also improve control of light absorption since light incidence angles on such surfaces is naturally aligned with three-dimensional nature of propagating light waves. In other embodiments, however, the annular chambers 102a-c may exhibit other cross-sectional shapes, without departing from the scope of the disclosure. Suitable cross-sectional shapes include, but are not limited to, oval, ovoid, polygonal (e.g., triangular, square, rectangular, etc.), polygonal with rounded corners, curvilinear (e.g., combination of curved and straight), convex, concave, convexo-concave, concavo-convex, or any combination thereof.

In some embodiments, the photobioreactor 100 may optionally include a scaffold 114 configured to secure and/or support the annular chambers 102a-c. In some embodiments, the scaffold 114 and the annular chambers 102a-c may be made of the same material and may otherwise comprise a monolithic structure, such as might be possible through a three-dimensional printing process. In other embodiments, however, the scaffold 114 and the annular chambers 102a-c may comprise separate structures. In the illustrated embodiment, the scaffold 114 defines an interior 116 sized to receive and support the annular chambers 102a-c.

The scaffold 114 may be made of any of the transparent or translucent, and rigid or semi-rigid materials mentioned above for the annular chambers 102a-c. In such embodiments, light may be able to penetrate (propagate) through the walls of the scaffold 114 at any angle to provide photonic energy input to the algae slurry 112 contained within the annular chambers 102a-c. In other embodiments, however, the scaffold 114 may be made of an opaque material that does not facilitate light penetration. In such embodiments, suitable light or light sources may be provided within the interior 116 of the scaffold 114 to provide the required photonic energy input to the algae slurry 112.

Referring specifically to FIG. 1A, the gaps 108a,b and the central opening 110 allow light 118 to penetrate between the annular chambers 102a-c along the entire height 104. The light 118 may originate from any source capable of providing the proper photonic energy to the algae slurry 112. For example, the light 118 may comprise natural sunlight, but may alternatively comprise a variety of artificial light sources including, but not limited to, light emitting diodes (LEDs), incandescent lights, lasers, a halogen light source, a bioluminescent light source, or any combination thereof.

In some embodiments, one or more light waveguides 120 may be arranged within the gaps 108a,b and/or the central opening 110 to help optimize light propagation into the annular chambers 102a-c and onto the algae slurry 112 along the entire height 104. In some embodiments, the light waveguides 120 may comprise individual structures placed periodically or intermittently within the gaps 108a,b. In other embodiments, however, the light waveguides 120 within the gaps 108a,b may comprise monolithic, annular chambers. The light waveguide 120 arranged within the central opening 110 may exhibit a generally conical shape.

In some embodiments, the light waveguides 120 may provide a reflective outer surface that substantially or fully reflects the incoming light 118. The reflective outer surface may comprise, for example, a mirror or a polished surface. In some embodiments, as illustrated, the light waveguides 120 may be angled outward along the height 104 and otherwise toward the inner sidewall of the radially adjacent annular chamber 102a-c. The angled outer surfaces of the waveguides 120 may help redirect the incidence angle of the incoming light 118 within the gaps 108a,b and the central opening 110 toward the inner sidewalls of the annular chambers 102a-c. More specifically, because the waveguides 120 are angled outward along the height 104 from top to bottom, any incoming light 118 that enters the gaps 108a,b impinges upon an angled surface and is directed radially outward toward the inner sidewall of the radially adjacent annular chamber 102a-c.

In the illustrated embodiment, the angled outer surfaces of the waveguides 120 are straight and extend at a constant angle along the height 104. In other embodiments, however, the angled outer surfaces of the waveguides 120 may be non-uniform (e.g., vary or undulate) along the height 104, without departing from the scope of the disclosure. As will be appreciated, the curved outer surfaces of the light waveguides 120 and the annular chambers 102a-c help optimize light incidence angles onto the algae contained in the annular chambers 102a-c.

In other embodiments, one or more of the light waveguides 120 may comprise an artificial light source that emits light toward the algae contained within the radially adjacent annular chamber 102a-c. In such embodiments, the light waveguides 120 may be configured to emit light in a wavelength suitable for the growth of the particular algae strain/species within the algae slurry 112. Suitable artificial light sources include any of those mentioned above as the source of the light 118.

In example operation of the photobioreactor 100, the annular chambers 102a-c may be filled at least partially with the algae slurry 112. Water and algae feedstock may be added to the annular chambers 102a-c via a liquid flow manifold 122a. As illustrated, the liquid flow manifold 122a includes one or more conduits (fluid lines) that are fluidly coupled at one or more locations to each annular chamber 102a-c to facilitate fluid transfer into each chamber 102a-c. In embodiments that include the scaffold 114, the liquid flow manifold 122a may further be fluidly coupled to a first coupling 124a secured to the body of the scaffold 114. The first coupling 124a may provide a coupling location where water and algae feedstock may be introduced into the photobioreactor 100 via the liquid flow manifold 122a.

A gas may be introduced into some or all of the annular chambers 102a-c via a gas flow manifold 122b, alternately referred to as a sparging mechanism. As illustrated, the gas flow manifold 122b includes one or more conduits (fluid lines) that are fluidly coupled at one or more locations to each annular chamber 102a-c to facilitate the transfer of one or more gases into each chamber 102a-c. The gas flow manifold 122b is further fluidly coupled to a second coupling 124b secured to the body of the scaffold 114. The second coupling 124b may provide a coupling location where gases may be introduced into the photobioreactor 100 via the gas flow manifold 122b.

The gas introduced into the annular chambers 102a-c may include, but is not limited to, air, carbon dioxide, nitrogen, or any combination thereof. The injected gas can serve two purposes. First, the gas can help agitate or mix the contents of the algae slurry 112 as it bubbles up and through each annular chamber 102a-c. Bubbling gas upward through the algae slurry 112 promotes fluid circulation and mass exchange across liquid-gas interfaces. Second, the gas can provide a feed substrate for the algae slurry 112. In such embodiments, the gas may include a larger ratio of carbon dioxide ($CO_2$), which is naturally consumed by the algae in the algae slurry 112. The $CO_2$ may come from any suitable source, including atmospheric air, an exhaust stream from a combustion process, a storage location including tanks or geological formations, or any combination thereof.

The algae in the algae slurry 112 also feeds on the incoming or generated light 118 via photosynthesis. As described above, light 118 is able to enter the gaps 108a,b between adjacent annular chambers 102a-c and the central opening 110 defined by the innermost annular chamber 102a. Moreover, the light waveguides 120 may help optimize light propagation into the algae slurry 112 along the entire height 104 of each annular chamber 102a-c. The algae slurry 112 may be exposed to the light 118 in the form of sunlight or artificial lights operating based on an illumination profile for a period of time, such as a day, multiple days, or even months.

As a by-product of photosynthesis, algae produces molecular oxygen ($O_2$) and removal of the $O_2$ can be beneficial or required for healthy algae growth. In embodiments where the annular chambers 102a-c are open-ended at the top, the generated $O_2$ may be naturally vented to the surrounding atmosphere. In embodiments where the annular chambers 102a-c are closed, however, generated gases (e.g., $O_2$) may be periodically or continually vented from the annular chambers 102a-c via a gas discharge manifold 122c. As illustrated, the gas discharge manifold 122c includes one or more conduits (fluid lines) that are fluidly coupled to the top of each annular chamber 102a-c to receive and discharge generated gases. The gas discharge manifold 122c is further fluidly coupled to a third coupling 124c secured to the body of the scaffold 114, which may provide a coupling location where generated gases may be discharged into the atmosphere or conveyed for downstream processing.

As the algae within the algae slurry 112 grow, the concentration of algae in each annular chamber 102a-c will increase. At some point, increased microorganism growth can result in reduced viability, due to overcrowding, reduced light access, reduced nutrient access, and combinations thereof. This can be addressed by periodically or continuously diluting the algae density in the annular chambers 102a-c to maintain it within acceptable levels. To accomplish this, flow through the liquid flow manifold 122a may be reversed using typical valving equipment and cycles to at least partially drain the algae slurry 112 from the annular chambers 102a-c. For example, after a certain amount growth, which can correspond to lowered optical transparency or heightened density of the algae slurry 112, drainage valves can be opened to allow the (now) algae-rich slurry to flow under gravity to central collection points. Subsequently, fresh supplies of nutrients and liquids are pumped in via the valving system.

While not shown, each of the manifolds 122a-c may include one or more valves used to control the influx and extraction of fluids (liquids and gases) throughout the photobioreactor 100. For example, one or more valves may be included in the liquid flow manifold 122a to control the timing and amount of water and algae feedstock added to the annular chambers 102a-c. Such valves may also be operated to control the timing and amount of the algae slurry 112 drained from the annular chambers 102a-c for harvesting the algae. One or more additional valves may be included in the gas flow manifold 122b to control the timing and amount of gas sparged into the annular chambers 102a-c. Furthermore, one or more additional valves may be included in the gas discharge manifold 122c to control the timing and amount of gases (e.g., O2) extracted from the annular chambers 102a-c. Some or all of the valves may be manually operated, as needed. However, operation of the some or all of the valves may alternatively be automated based on sensed operational parameters of the photobioreactor 100. In such embodiments, the photobioreactor 100 may include an automated system (e.g., a computer system) that monitors flow rates and total volumes within the annular chambers 102a-c, and may actuate valves, pumps, and associated components to adjust flows, control algae growth, and maintain proper fluid levels.

Figure 2:
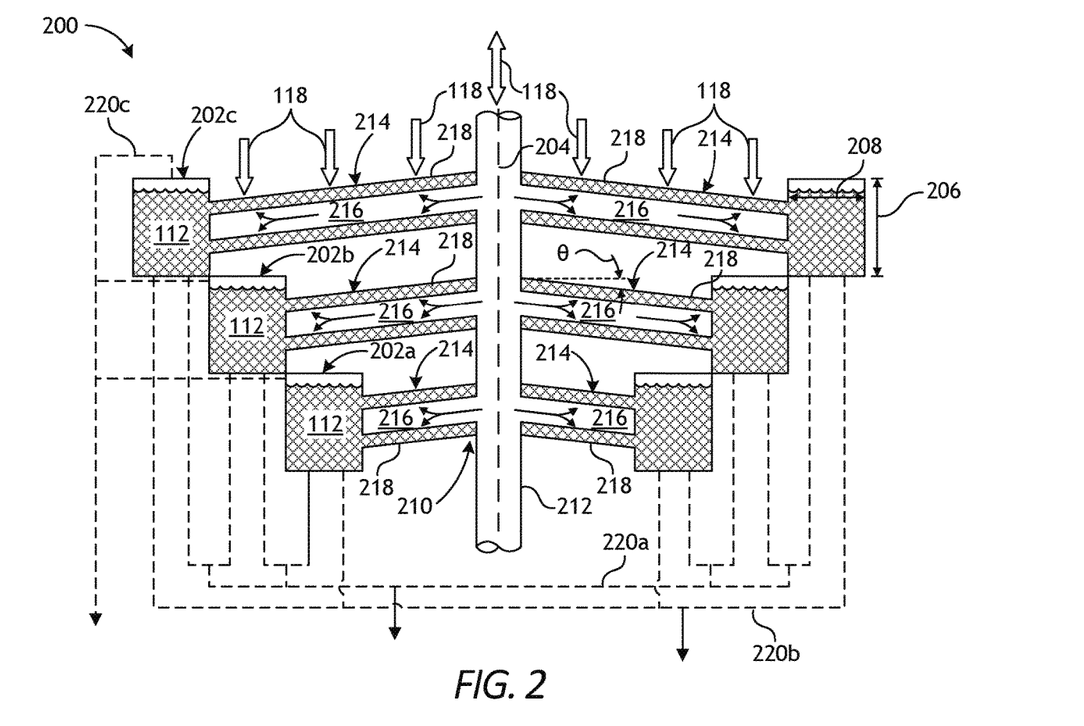
FIG. 2 is a cross-sectional side view of another example photobioreactor that may incorporate the principles of the present disclosure.

FIG. 2 is a cross-sectional side view of another example photobioreactor 200 that may incorporate the principles of the present disclosure. The photobioreactor 200 is similar in some respects to the photobioreactor 100 of FIG. 1 and therefore will be best understood with reference thereto, were like numerals will represent like components not described again. Similar to the photobioreactor 100, the photobioreactor 200 may be configured to cultivate, grow, and harvest algae to be converted into biofuels. As illustrated, the photobioreactor 200 includes or otherwise defines a plurality of annular chambers, shown as a first annular chamber 202a, a second annular chamber 202b, and a third annular chamber 202c. While the photobioreactor 200 is described herein as including three annular chambers 202a-c, more or less than three annular chambers 202a-c may be employed in the photobioreactor 200, without departing from the scope of the disclosure.

In the illustrated embodiment, the annular chambers 202a-c comprise cylindrical structures that are concentrically arranged about a central axis 204 and at least partially radially and axially offset from each other along the central axis 204. More specifically, the first annular chamber 202a is radially and axially offset from the second annular chamber 202b, and the second annular chamber 202b is radially and axially offset from the third annular chamber 202c. In some embodiments, as illustrated, the annular chambers 202a-c may be radially and axially offset from each other such that no part of one annular chamber 202a-c overlaps with any axial or radial portion of another annular chamber 202a-c. This may prove advantageous in maximizing light exposure to the algae slurry 112 by not creating structural shadows on adjacent annular chambers 202a-c. In other embodiments, however, the annular chambers 202a-c may be radially and/or axially offset from each other such that a portion of at least one annular chamber 202a-c radially and/or axially overlaps with a portion of one of the other annular chambers 202a-c, without departing from the scope of the disclosure.

Each annular chamber 202a-c exhibits a height 206 and a depth 208 (i.e., the distance between inner and outer radial surfaces). In some embodiments, the height 206 of each annular chamber 202a-c may be the same. In other embodiments, however, the height 206 of one or more of the annular chambers 202a-c may be different. Similarly, in some embodiments, the depth 208 of each annular chamber 202a-c may be the same, but in other embodiments the depth 208 of one or more of the annular chambers 202a-c may be different, without departing from the scope of the disclosure.

Specific dimensions of any of the structural components of the photobioreactor 200 can vary and will generally depend on the specific application and desired operating parameters of the photobioreactor 200. Accordingly, the diameter, the height 206, and the depth 208 of any of the annular chambers 202a-c can be varied and otherwise optimized to meet specific operating parameters or desired outcomes. Accordingly, nothing in this disclosure should be interpreted as limiting the size or dimensions of any of the structural components of the photobioreactor 200.

Similar to the annular chambers 102a-c of FIGS. 1A-1B, the algae slurry 112 may be contained within each annular chamber 202a-c. Moreover, the annular chambers 202a-c may be made of any transparent or translucent material mentioned above for the annular chambers 102a-c. In the illustrated embodiment, the annular chambers 202a-c exhibit a circular cross-section, but could alternatively exhibit other cross-sectional shapes including, but not limited to, oval, ovoid, polygonal (e.g., triangular, square, rectangular, etc.), polygonal with rounded corners, curvilinear (e.g., combination of curved and straight), convex, concave, convexo-concave, concavo-convex, or any combination thereof.

In the illustrated embodiment, the photobioreactor 200 further includes a scaffold 210, and the annular chambers 202a-c may be at least partially supported by the scaffold 210. As illustrated, the scaffold 210 may include a central support 212 extending along the central axis 204 and one or more spindles 214 extending radially between the central support 212 and each annular chamber 202a-c. In the illustrated embodiment, the central support 212 and the spindles 214 each exhibit a circular cross-section, but could alternatively exhibit other cross-sectional shapes including, but not limited to, oval, ovoid, polygonal (e.g., triangular, square, rectangular, etc.), polygonal with rounded corners, curvilinear (e.g., combination of curved and straight), convex, concave, convexo-concave, concavo-convex, or any combination thereof.

At any given elevation along the central axis 204, the spindles 214 supporting a given annular chamber 202a-c may be equidistantly or non-equidistantly spaced about the central support 212. Moreover, in some embodiments, spindles 214 positioned at higher elevations along the central axis 204 may be angularly offset from spindles 214 positioned at lower elevations along the central axis 204. This may prove advantageous in eliminating shadows that might be cast on lower spindles 214, and thereby maximizing light 118 exposure on the lower spindles 214.

In some embodiments, one or more of the spindles 214 may be at least partially Tillable with the algae slurry 112 and in fluid communication with the adjacent annular chamber 202a-c. For example, in at least one embodiment, one or more of the spindles 214 may comprise a pipe or tube that may be at least partially filled with the algae slurry 112 and free to flow between the spindle 214 and the associated annular chamber 202a-c to which it is attached. In the illustrated embodiment, however, each spindle 214 defines a hollow section 216 surrounded by an annular cavity 218. The annular cavity 218 may be in fluid communication with the annular chamber 202a-c to which the corresponding spindle 214 is attached. In such embodiments, the algae slurry 112 may be free to flow between the annular chamber 202a-c and the annular cavity 218 of the spindle 214.

In some embodiments, the central support 212 may comprise a light pipe capable of collecting or channeling light 118 (e.g., broad spectrum sunlight) in either direction along the central axis 204. The light pipe may operate with total internal reflection (TIR) to convey the light 118. In such embodiments, the hollow section 216 of one or more of the spindles 214 may be in communication with the light pipe and capable of receiving the light 118 from the central support 212 and irradiating the algae slurry 112 contained within the associated annular cavity 218. In other embodiments, however, one or both of the central support 212 and the spindles 214 may comprise or otherwise include an artificial light source capable of generating the light 118. In such embodiments, the central support 212 and/or and the spindles 214 may comprise any of the artificial light sources mentioned herein and capable of providing photonic energy to the algae slurry 112.

The central support 212 and the spindles 214 may be made of any of the rigid or semi-rigid materials mentioned herein. Moreover, in some embodiments, the central support 212 and/or the spindles 214 may be made of any of the transparent or translucent materials mentioned herein for the annular chambers 102a-c. In such embodiments, light 118 may be able to penetrate (propagate) through the walls of the spindles 214 at any angle to provide photonic energy input to the algae slurry 112 contained within the annular cavities 218. In other embodiments, however, the scaffold 210 may be made of an opaque material that does not facilitate light penetration. In such embodiments, suitable light or light sources may be provided within the hollow sections 216 of each spindle 214 to irradiate the algae slurry 112 contained within the associated annular cavities 218.

In some embodiments, as illustrated, one or more of the spindles 214 may be angled downwardly at an angle Θ relative to horizontal (i.e., perpendicular to the central axis 204). Angling the spindles 214 downwardly may prove advantageous in allowing gravity to help drain the algae slurry 112 within the annular cavities 218 into the corresponding annular chambers 202a-c. The angle Θ may range between about 5° and about 35°.

In some embodiments, the cross-section of one or more of the spindles 214 may taper in the radially outward direction. More specifically, the cross-section of at least one of the spindles 214 may be larger where it is coupled to the central support 212 as compared to where it is coupled to the corresponding annular chamber 202a-c. Accordingly, such spindles 214 may be characterized as tapering in the radially outward direction. Tapering the spindles 214 may prove advantageous in reducing and minimizing shadows on the boundary surfaces of the annular chambers 202a-c and the spindles 214 located at lower elevations. The embodiment depicted in FIG. 2 is a similitude of one of Earth's original photobioreactors, namely, the tree. In trees, branches (analogous to the spindles 114) deploy outward as spokes but with an upward slope/angle, to balance gravity forces with light-catching needs. In the case of FIG. 2, since the supply of nutrients to the "branches" of the artificial tree is from the outer circumference, the slope is accordingly downward.

In example operation of the photobioreactor 200, the annular chambers 202a-c and the annular cavities 218 (if applicable) may be filled at least partially with the algae slurry 112. Water and algae feedstock may be added to the annular chambers 202a-c and the annular cavities 218 (if applicable) via a liquid flow manifold 220a. As illustrated, the liquid flow manifold 220a includes one or more conduits (fluid lines) that are fluidly coupled at one or more locations to each annular chamber 202a-c to facilitate fluid transfer into each chamber 202a-c.

A gas may be introduced into some or all of the annular chambers 202a-c via a gas flow manifold 220b, alternately referred to as a sparging mechanism. As illustrated, the gas flow manifold 220b includes one or more conduits (fluid lines) that are fluidly coupled to each annular chamber 202a-c in one or more locations to facilitate the transfer of one or more gases into each chamber 202a-c. The gas introduced into the annular chambers 202a-c may include, but is not limited to, air, carbon dioxide, and nitrogen.

The algae in the algae slurry 112 also feeds on the incoming or generated light 118 via photosynthesis. As described above, light 118 may be able to impinge upon the algae slurry 112 within the annular cavities 218 on the exterior, but also the interior via light 118 propagating within (or emitted from) the hollow space 216 defined within the spindles 214. The algae slurry 112 may be exposed to the light 118 in the form of sunlight or artificial lights operating based on an illumination profile for a period of time, such as a day, multiple days, or even months.

The molecular oxygen (O2) generated as a by-product of photosynthesis of the algae slurry 112 may be naturally vented to the surrounding atmosphere in embodiments where the annular chambers 202a-c are open-ended at the top. In embodiments where the annular chambers 202a-c are closed, however, generated gases (e.g., O2) may be periodically or continually vented from the annular chambers 202a-c via a gas discharge manifold 220c. As illustrated, the gas discharge manifold 220c includes one or more conduits (fluid lines) that are fluidly coupled at one or more locations near the top of each annular chamber 202a-c to receive and discharge gases.

As the algae within the algae slurry 112 grow, the concentration of algae in each annular chamber 202a-c will increase. At some point, increased microorganism growth can result in reduced viability, due to crowding, reduced light access, reduced nutrient access, and combinations thereof. This can be addressed by periodically or continuously diluting the algae density in the annular chambers 202a-c to maintain it within acceptable levels. To accomplish this, flow through the liquid flow manifold 220a may be reversed using typical valving equipment and cycles to at least partially drain the algae slurry 112 from the annular chambers 202a-c. For example, after a certain amount growth, which can correspond to lowered optical transparency or heightened density of the algae slurry 112, drainage valves can be opened to allow the (now) algae-rich slurry to flow under gravity to central collection points. Subsequently, fresh supplies of nutrients and liquids are pumped in via the valving system.

While not shown, each of the manifolds 220a-c may include one or more valves used to control the influx and extraction of fluids (liquids and gases) throughout the photobioreactor 200, as similarly described above with reference to the valving of photobioreactor 100 of FIGS. 1A-1B.

Referring again to FIG. 1A, in some embodiments, one or more of the waveguides 120 positioned within the gaps 108a,b and the central aperture 110 may comprise a periodic structure or a structure that defines periodic surfaces. Forming the waveguides 120 as periodic structures or defining periodic surfaces may improve the strength of the photobioreactor 100 and may also improve light scattering properties that allow the waveguides 120 to function as prismatic filters of the light 118 or as light pipes. In such embodiments, the waveguides 120 may be formed as or comprising singly periodic surfaces/structures, doubly periodic surfaces/structures, or triply periodic surfaces/structures.

Figure 3A:
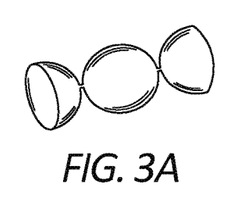
FIGS. 3A-3C depict examples of singly periodic structures of which the waveguides of FIGS. 1A-1B may be formed or include.
Figure 3B:
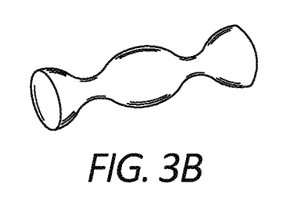
Figure 3C:
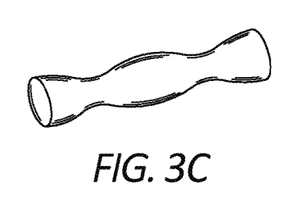
Figure 4A:
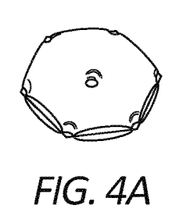
FIGS. 4A-4E depict examples of doubly periodic structures of which the waveguides of FIGS. 1A-1B may be formed or include.
Figure 4B:
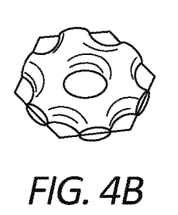
Figure 4C:
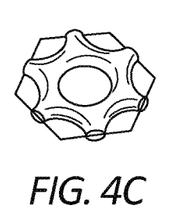
Figure 4D:
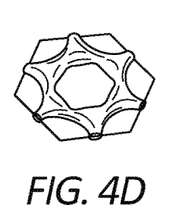
Figure 4E:
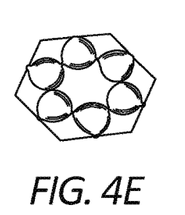
Figure 5A:
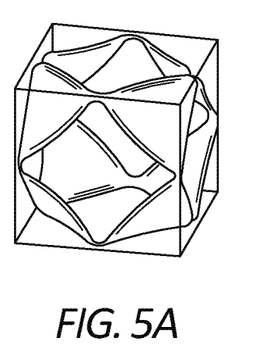
FIGS. 5A-5E depict examples of triply periodic structures of which the waveguides of FIGS. 1A-1B may be formed or include.
Figure 5B:
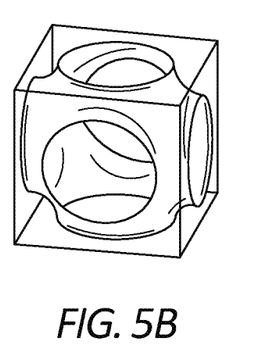
Figure 5C:
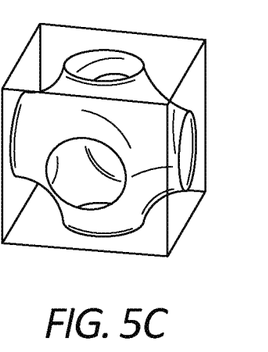
Figure 5D:
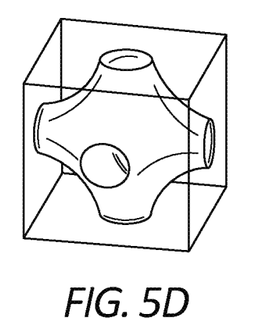
Figure 5E:
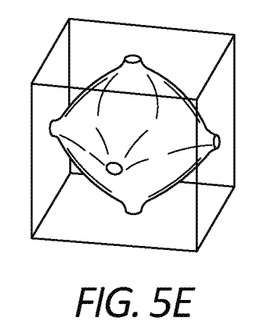

FIGS. 3A-3C depict examples of singly periodic structures of which the waveguides 120 of FIGS. 1A-1B may be formed or otherwise include. As illustrated, the singly periodic structures can periodically transition between a sphere or bulbous section and a cylinder. Typically, a singly periodic structure exhibits a periodicity along a single axis. This periodicity in the surface can be, for example, a regular undulation or curvature that repeats exactly. For the purposes of light waveguides, the singly periodic surface introduces additional curved surface to a normal cylindrical surface with parallel sides. In extreme cases, such as shown in FIG. 3A, the waveguide deployment generates near spherical shapes which coincide with optimal light incidence surface angles, since light expands in a spherical manner.

FIGS. 4A-4E depict examples of doubly periodic structures of which the waveguides 120 of FIGS. 1A-1B may be formed or otherwise include, and FIGS. 5A-5E depict examples of triply periodic structures of which the waveguides 120 of FIGS. 1A-1B may be formed or otherwise include. Doubly periodic structures approach two families of orthogonal planes, and triply periodic structures are minimal structures in three dimensions in R3 that is invariant under a rank-3 lattice of translations. Triply periodic structures have the symmetries of a crystallographic group, such as cubic, tetragonal, rhombohedral, and orthorhombic symmetries. Doubly and triply periodic surfaces possess additional axes of periodicity (i.e., in the Y and Z directions), which are therefore capable of introducing additional surface features. In addition, all such periodic surfaces can be mass-produced efficiently with modern 3D printing techniques. One advantage of triply periodic surfaces is their ability to provide minimal surfaces, which minimize the volume of material for the surface provided. This occurs in a variety of examples in nature, including butterfly wings, which have remarkable resilience yet are extremely lightweight. This feature is advantageous for increasing photobioreactor wall strength while using only minimal amount of material, which latter also maintains light absorption and control.

Embodiments

The present disclosure provides, among others, the following embodiments, each of which may be considered as optionally including any alternate embodiments.

Clause 1. A photobioreactor that includes one or more annular chambers concentrically positioned about a central axis, and an algae slurry contained within the one or more annular chambers.

Clause 2. The photobioreactor of Clause 1, wherein the one or more annular chambers are made of a transparent or translucent material selected from the group consisting of glass, a polymer, acrylic, a composite material, and any combination thereof.

Clause 3. The photobioreactor of Clause 1 or 2, wherein the one or more annular chambers exhibit a cross-section selected from the group consisting of circular, oval, ovoid, polygonal, polygonal with rounded corners, curvilinear, convex, concave, convexo-concave, concavo-convex, and any combination thereof.

Clause 4. The photobioreactor of any of Clauses 1 to 3, further comprising:
a liquid flow manifold fluidly coupled to the one or more annular chambers to introduce water and algae feedstock to the one or more annular chambers; and
a gas flow manifold fluidly coupled to the one or more annular chambers to introduce a gas into the one or more annular chambers.

Clause 5. The photobioreactor of any of Clauses 1 to 4, further comprising a gas discharge manifold fluidly coupled to the one or more annular chambers to receive and discharge gases generated by algae within the algae slurry.

Clause 6. The photobioreactor of any of Clauses 1 to 5, wherein the one or more annular chambers comprise:
a first annular chamber that defines a central opening; and
a second annular chamber radially offset from the first annular chamber such that a gap is defined between the first and second annular chambers.

Clause 7. The photobioreactor of any of Clauses 1 to 6, further comprising one or more light waveguides arranged within at least one of the central opening and the gap.

Clause 8. The photobioreactor of any of Clauses 1 to 7, wherein the one or more light waveguides provide a reflective outer surface.

Clause 9. The photobioreactor of any of Clauses 1 to 8, wherein the one or more light waveguides are angled top to bottom toward an inner sidewall of a radially adjacent annular chamber to redirect a light incidence angle toward the inner sidewall of the radially adjacent annular chamber.

Clause 10. The photobioreactor of any of Clauses 1 to 7, wherein the one or more light waveguides comprise an artificial light source.

Clause 11. The photobioreactor of any of Clauses 1 to 7, wherein the one or more light waveguides comprise a periodic structure or defines periodic surfaces.

Clause 12. The photobioreactor of any of Clauses 1 to 5, wherein the one or more annular chambers comprise:
a first annular chamber; and
a second annular chamber radially and axially offset from the first annular chamber along the central axis.

Clause 13. The photobioreactor of any of Clauses 1 to 5 and 12, further comprising a scaffold that at least partially supports the one or more annular chambers and includes:
a central support extending along the central axis; and
one or more spindles extending radially between the central support and the first and second annular chambers.

Clause 14. The photobioreactor of any of Clauses 1 to 5 and 12 to 13, wherein at least one of the one or more spindles is at least partially Tillable with the algae slurry and in fluid communication with one of the first or second annular chambers.

Clause 15. The photobioreactor of any of Clauses 1 to 5 and 12 to 14, wherein the central support comprises a light pipe and at least one of the one or more spindles defines a hollow section in communication with the light pipe to receive light conveyed within the light pipe to irradiate the algae slurry along the at least one of the one or more spindles.

Clause 16. The photobioreactor of any of Clauses 1 to 5 and 12 to 13, wherein at least one of the central support and the one or more spindles comprises an artificial light source.

Clause 17. A method of growing algae for biofuel production that includes introducing an algae slurry into one or more annular chambers concentrically positioned about a central axis of a photobioreactor, introducing a gas into the one or more annular chambers via a gas flow manifold fluidly coupled to the one or more annular chambers, and impinging light on the algae slurry contained within the one or more annular chambers.

Clause 18. The method of Clause 17, wherein the one or more annular chambers include a first annular chamber that defines a central opening, and a second annular chamber radially offset from the first annular chamber such that a gap is defined between the first and second annular chambers, the method further comprising directing the light into the central opening and the gap.

Clause 19. The method of Clauses claim 17 or 18, wherein one or more light waveguides are arranged within at least one of the central opening and the gap and the one or more light waveguides are angled top to bottom toward an inner sidewall of a radially adjacent annular chamber, the method further comprising:

redirecting a light incidence angle of the light toward the inner sidewall of the radially adjacent annular chamber with the one or more light waveguides.

Clause 20. The method of any of Clauses 17 to 19, wherein the one or more annular chambers include a first annular chamber, and a second annular chamber radially and axially offset from the first annular chamber along the central axis.

Clause 21. The method of any of Clauses 17 to 20, wherein a scaffold at least partially supports the one or more annular chambers and includes a central support extending along the central axis, and one or more spindles extending radially between the central support the one or more annular chambers.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A photobioreactor, comprising:
one or more annular chambers concentrically positioned about a central axis,
wherein the one or more annular chambers comprise:
a first annular chamber that defines a central opening; and
a second annular chamber radially offset from the first annular chamber such that a gap is defined between the first and second annular chambers, and
wherein one or more light waveguides providing a reflective outer surface are arranged within at least one of the central opening and the gap, the arrangement being angled top to bottom toward an inner sidewall of a radially adjacent annular chamber to redirect a light incidence angle toward the inner sidewall of the radially adjacent annular chamber; and
an algae slurry contained within the one or more annular chambers.

2. The photobioreactor of claim 1, wherein the one or more annular chambers are made of a transparent or translucent material selected from the group consisting of glass, a polymer, acrylic, a composite material, and any combination thereof.

3. The photobioreactor of claim 1, wherein the one or more annular chambers exhibit a cross-section selected from the group consisting of circular, oval, ovoid, polygonal, polygonal with rounded corners, curvilinear, convex, concave, convexo-concave, concavo-convex, and any combination thereof.

4. The photobioreactor of claim 1, further comprising:
a liquid flow manifold fluidly coupled to the one or more annular chambers to introduce water and algae feedstock to the one or more annular chambers; and
a gas flow manifold fluidly coupled to the one or more annular chambers to introduce a gas into the one or more annular chambers.

5. The photobioreactor of claim 4, further comprising a gas discharge manifold fluidly coupled to the one or more annular chambers to receive and discharge gases generated by algae within the algae slurry.

6. The photobioreactor of claim 1, wherein the one or more light waveguides comprise an artificial light source.

7. The photobioreactor of claim 1, wherein the one or more light waveguides comprise a periodic structure or defines periodic surfaces.

8. A method of growing algae for biofuel production, comprising:
introducing an algae slurry into one or more annular chambers concentrically positioned about a central axis of a photobioreactor,
wherein the one or more annular chambers comprise:
a first annular chamber that defines a central opening; and
a second annular chamber radially offset from the first annular chamber such that a gap is defined between the first and second annular chambers, and
wherein one or more light waveguides providing a reflective outer surface are arranged within at least one of the central opening and the gap, the arrangement being angled top to bottom toward an inner sidewall of a radially adjacent annular chamber to redirect a light incidence angle toward the inner sidewall of the radially adjacent annular chamber;
introducing a gas into the one or more annular chambers via a gas flow manifold fluidly coupled to the one or more annular chambers; and
impinging light on the algae slurry contained within the one or more annular chambers.

9. The method of claim 8, further comprising directing the light into the central opening and the gap.

10. The method of claim 9, further comprising:
redirecting a light incidence angle of the light toward the inner sidewall of the radially adjacent annular chamber with the one or more light waveguides.

11. The method of claim 4, wherein the gas is selected from the group consisting of air, carbon dioxide, nitrogen, and any combination thereof.

12. The method of claim 8, further comprising a liquid flow manifold fluidly coupled to the one or more annular chambers to introduce the algae slurry to the one or more annular chambers.

13. The method of claim 8, wherein the one or more light waveguides comprise an artificial light source.

14. The method of claim 8, wherein the one or more light waveguides comprise a periodic structure or defines periodic surfaces.

15. The method of claim 8, wherein the gas is selected from the group consisting of air, carbon dioxide, nitrogen, and any combination thereof.

16. The method of claim 8, further comprising a gas discharge manifold fluidly coupled to the one or more annular chambers to receive and discharge gases generated by algae within the algae slurry.

17. The method of claim 16, further comprising receiving and discharging a gas through the gas discharge manifold.

* * * * *